United States Patent
Ogawa et al.

(10) Patent No.: US 7,808,620 B2
(45) Date of Patent: Oct. 5, 2010

(54) MICROCHIP TESTING DEVICE

(75) Inventors: Yoshimasa Ogawa, Himeji (JP);
Katsuoki Miyasu, Himeji (JP);
Yoshihiko Okumura, Himej (JP)

(73) Assignee: Ushiodenki Kabushiki Kaisha, Tokyo (JP)

( * ) Notice: Subject to any disclaimer, the term of this patent is extended or adjusted under 35 U.S.C. 154(b) by 0 days.

(21) Appl. No.: 12/401,888

(22) Filed: Mar. 11, 2009

(65) Prior Publication Data

US 2009/0244539 A1    Oct. 1, 2009

(30) Foreign Application Priority Data

Mar. 26, 2008    (JP) .............................. 2008-080715

(51) Int. Cl.
*G01J 5/48* (2006.01)
(52) U.S. Cl. .................... 356/44; 356/439; 356/440; 362/269; 362/247; 362/285
(58) Field of Classification Search ............... 356/439, 356/440, 44; 362/269, 249.01, 247, 285, 362/362
See application file for complete search history.

(56) References Cited

U.S. PATENT DOCUMENTS 4,076,420 A  *  2/1978  De Maeyer et al. ......... 356/320

| | | | |
|---|---|---|---|
| 5,343,370 A | | 8/1994 | Ohashi et al. |
| 5,397,966 A | | 3/1995 | Vrionis et al. |
| 7,545,087 B2 | * | 6/2009 | Miyasu et al. ................ 313/24 |

FOREIGN PATENT DOCUMENTS

| | | |
|---|---|---|
| EP | 1 862 792 A2 | 12/2007 |
| JP | 2005-245473 A | 9/2005 |
| JP | 2007-225479 A | 9/2007 |

* cited by examiner

*Primary Examiner*—Gregory J Toatley, Jr.
*Assistant Examiner*—Iyabo S Alli
(74) *Attorney, Agent, or Firm*—Roberts Mlotkowski; Safran & Cole, P.C.; David S. Safran

(57) ABSTRACT

A testing device equipped with: a microchip having a receiver for a test fluid, a discharge lamp which emits light into the microchip test fluid receiver, a light source housing in which the discharge lamp is located, and an arithmetic calculation mechanism, which calculates the concentration of the component to be detected, based on the intensity of the light emitted from the test fluid container unit. To reduce the size of the device and to shield the arithmetic calculation mechanism from electromagnetic waves generated around the light source, the light source housing is equipped with shielding connected to the ground on the outside of the light source housing made of insulating material. The light source housing is positioned within an enclosure of the testing device holding the microchip and containing the arithmetic calculation mechanism, analysis output device(s), and other components of the testing device.

7 Claims, 11 Drawing Sheets

A-A' Cross section view

Fig. 7(a)
Fig. 7(b)
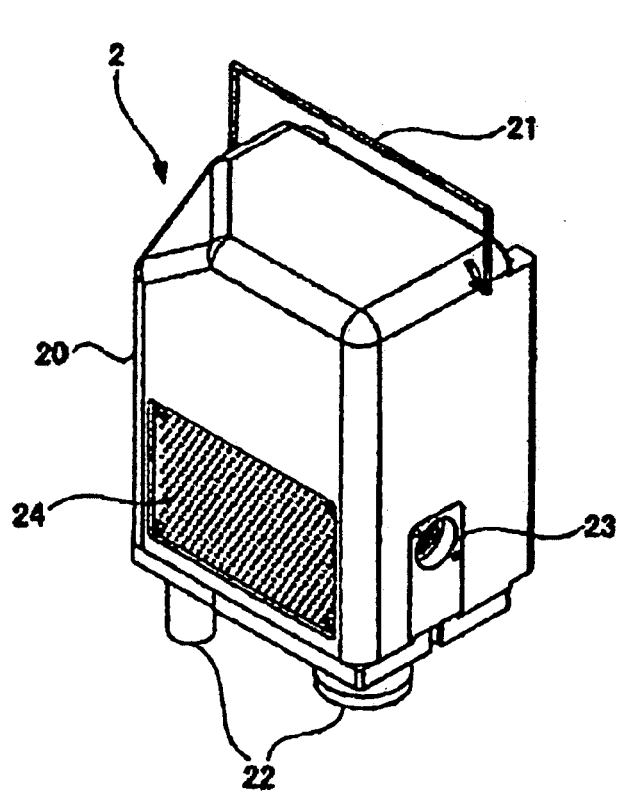
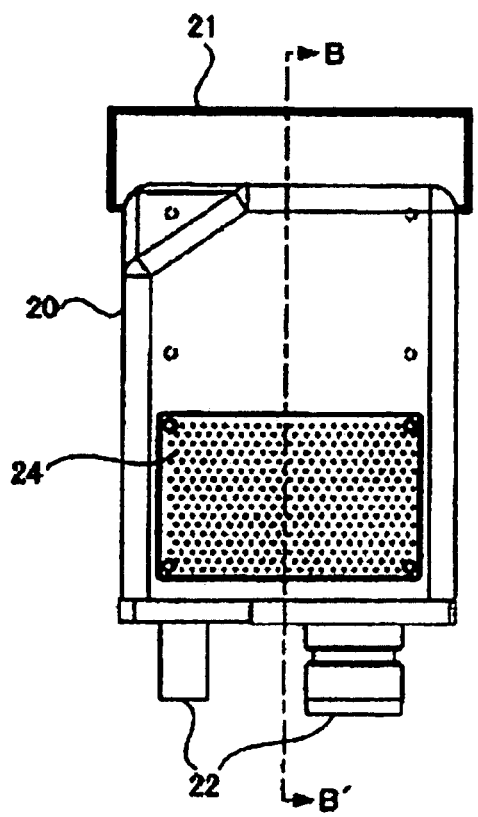
Fig. 7(c)
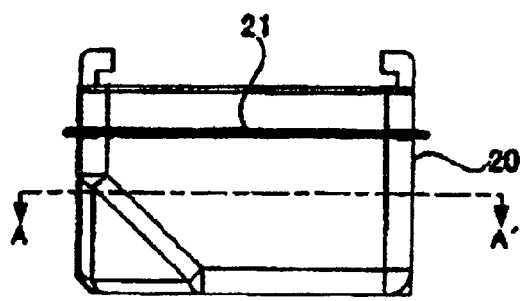

< A-A' Cross section view >

< B-B' Cross section view >

MICROCHIP TESTING DEVICE

BACKGROUND OF THE INVENTION

1. Field of Invention

The present invention relates to a testing device, which uses a microchip to identify the component to be detected to measure the concentration of the component to be detected in the liquid sample of the object to be measured by absorbance determination. More specifically, this invention relates to a testing device used to measure the activity of the enzymes necessary to diagnose human liver function, such as GPT (glutamate pyruvate transaminase) and γ-GTP (γ-glutamyl-transpeptidase).

2. Description of Related Art

The analysis method adapting micro-machine technology, which uses p-TAS (μ-Total Analysis System) and which performs more refined chemical analysis as compared to the conventional devices, and a microchip called "Lab on a chip," has attracted attention in recent years. Such technology is disclosed in Japanese published unexamined application 2007-225479. Analysis using such microchips aims to perform all analyzing processes, such as mixing, reaction, separation, extraction, and detection of the reagents, in micro-channels formed on a small substrate using micro-machine production technology. For example, this system is used in blood analysis and biomolecular analyses, such as the analysis of ultra-trace amounts of protein and nucleic acids, in the medical field.

The absorption photometry is frequently used to determine the quantity of the extracts or reactive organisms in the device using μ-TAS (referred to as the "testing device" hereinafter). The microchip is structured such that the samples to be tested and reagents to detect the information of the aforementioned test sample are contained in separate sites and the test fluid obtained by mixing test sample and reagent is filled in a very small test fluid receiver having a cross section $\phi$ of about 0.01 to 5 $mm^2$. In the actual analysis, light having a wavelength, which is absorbed by the test fluid, is emitted into the test fluid receiver and the amount of the light absorbed by the test fluid is measured to detect the concentration of the component of the test sample.

Ideally, lasers may be used since a discharge lamp of the testing device must emit light with high parallelism into the microchip test fluid receiver. However, it is necessary to use light with different wave lengths for the analysis of different test samples. Therefore, when only one device is intended to be used to analyze more than one sample, it is necessary to provide different types of lasers having specific wave lengths according to the types of the samples. This may cause some disadvantages, such as the increase in the size of the device as well as the increase of the cost. On the other hand, when a continuous light emitting lamp, such as a xenon lamp, is used as the discharge lamp along with a wavelength selecting device, the above mentioned disadvantages, such as the increase in the size of the device and the increase of the cost, can be avoided, since light with different wavelengths can be selected according to each sample.

Also in recent years, the POCT (Point of Care Testing), which conducts quick and highly precise analysis, is frequently performed in the clinical settings, such as in hospitals or clinics, emergency spots, and at home. In order to perform the POCT using the above mentioned testing device, it is required that the testing device be compact/simple and an easy to handle unit, since it is carried to the site where the diagnosis is to be performed. In addition, when the testing device adapting the μ-TAS is used, it is required that the intensity of the light emitted from the discharge lamp be high, since the light emitted from the discharge lamp must be lead to the narrow light path to reach into the microchip test fluid receiver. In other words, measurement errors can be minimized by increasing the intensity of the light emitted into the test fluid container unit. Based on these conditions, it is necessary that the brightness of the discharge lamp used in the testing device be high.

However, when the intensity of the light emitted form the discharge lamp is increased, the electromagnetic waves emitted around the discharge lamp may become so large as to cause malfunctioning of the precision apparatus of the testing device, and accurate analysis cannot be performed, especially when the rated wattage is raised to increase the brightness of the discharge lamp as described above; it becomes clear that adverse effects of the electromagnetic waves generated around the discharge lamp on the precision apparatus will increase and there will be higher chances of malfunction of the precision apparatus.

Installation of a shielding board between the image processing device and the discharge lamp in order to control the influence of the electromagnetic waves, which are emitted around the discharge lamp of the endoscopical device, on the precision apparatus is disclosed in Japanese published unexamined application 2005-245473. However, it is required to simplify and to reduce the size of the testing device used in the POCT as described above. Therefore, it is not desirable to adapt the technology described in Japanese published unexamined application 2005-245473, since it opposes these requirements.

SUMMARY OF THE INVENTION

Accordingly, an object of the present invention is to reduce the size of a test device of the type described above and to shield the electromagnetic waves generated around the light source when the brightness of the light source is increased in the testing device to analyze test samples.

Reducing the Size of the Testing Device

In the testing device of this invention, high voltage of several tens of kV must be applied to the discharge lamp at the time of lighting. In order to prevent leaks of the high voltage to the light source housing, which contains the discharge lamp, the light source housing needs to be insulated from the discharge lamp. Therefore, when the light source housing is made of metal, the light source housing must be made larger to make the insulation distance from the discharge lamp longer. However, it is required that the testing device using μ-TAS be small and easy to handle, and the size of the light source housing should not be large even to maintain enough insulating distance. But, it is possible to ensure that the light source housing is insulated from the discharge lamp, even when the size of the light source housing is smaller relative to the discharge lamp, by making the chassis unit, which is the main part of the light source housing, of insulating materials. In other words, it is possible to reduce the size of the testing device when the size of the light source housing is made smaller by using insulating materials to make it, since it will ensure the insulation between the container of the light source and the discharge lamp.

Shielding Electromagnetic Waves

When insulating materials are used to construct the light source housing as described above, the electromagnetic waves emitted around the discharge lamp cannot be shielded by the container unit of the light source, unlike when it is made of metal. Therefore, in order to completely shield the electromagnetic waves emitted from the discharge lamp, a shielding mechanism, which shields the electromagnetic waves, should be installed outside of the light source housing made of insulating materials.

The present invention was completed based on the above mentioned conditions, and is about:

the testing device equipped with: the microchip having a test fluid container unit, which contains a test fluid; a discharge lamp which emit light into the above mentioned microchip test fluid receiver; the light source housing in which the aforementioned discharge lamp is placed; and an arithmetic calculation mechanism, which calculates the concentration of the component to be detected, based on the intensity of the light emitted from the test fluid container unit, wherein the above mentioned light source housing is characterized by the fact that it is equipped with a shielding mechanism connected to the ground, which shields the electromagnetic waves emitted from the above mentioned light source outside the housing made of insulating material.

Further, this invention is characterized by the fact that the above mentioned shielding mechanism is a thin metal film placed on the outer surface of the above mentioned housing.

Further, the testing device of this invention is characterized by the fact that it is equipped with a pressing mechanism, which presses the area where the above mentioned thin metal film is formed in the outer surface of the above mentioned housing.

Additionally, this invention is characterized by the fact that the above mentioned pressing mechanism is connected to the ground.

Still further, the testing device of this invention is characterized by the fact that it is equipped with a cooling air supply mechanism, which supplies cooling air into the light source housing, wherein the cooling air inlet and the cooling air outlet are formed in the light source housing.

Furthermore, this invention is characterized by the fact that the above mentioned light source is a discharge lamp equipped with a light emitting unit, in which a pair of electrodes and a discharge gas is contained, and a bypass unit, which is connected to the both ends of the aforementioned light emitting unit; wherein the central axis of the discharge lamp is placed in a way that it is perpendicular to the ground.

Also, this invention is characterized by the fact that the light source housing is placed such that the above mentioned cooling air inlet is placed on the opposite side of the bypass unit, which is located vertically below the discharge lamp, and the cooling air outlet is placed on the opposite side of the bypass unit, which is located vertically above the discharge lamp.

EFFECTS OF THE INVENTION

In the light source housing according to the testing device of this invention, the shielding mechanism, which shields the electromagnetic waves emitted from the discharge lamp, is installed outside the housing made with insulating materials. Therefore, even though the light source housing is small relative to the discharge lamp, it is possible not only to insulate the light source housing from the discharge lamp, but also to shield the electromagnetic waves emitted around the discharge lamp by the shielding mechanism installed outside the housing. Accordingly, it is possible to reduce the size of the testing device, as well as to solve the problem of the malfunctioning of the precision apparatus.

BRIEF DESCRIPTION OF THE DRAWINGS

FIGS. 7(a)-(c) are perspective, front, and top views of the discharge lamp and the light source housing used in the testing device of this invention.

DETAILED DESCRIPTION OF THE INVENTION

Figure 1:
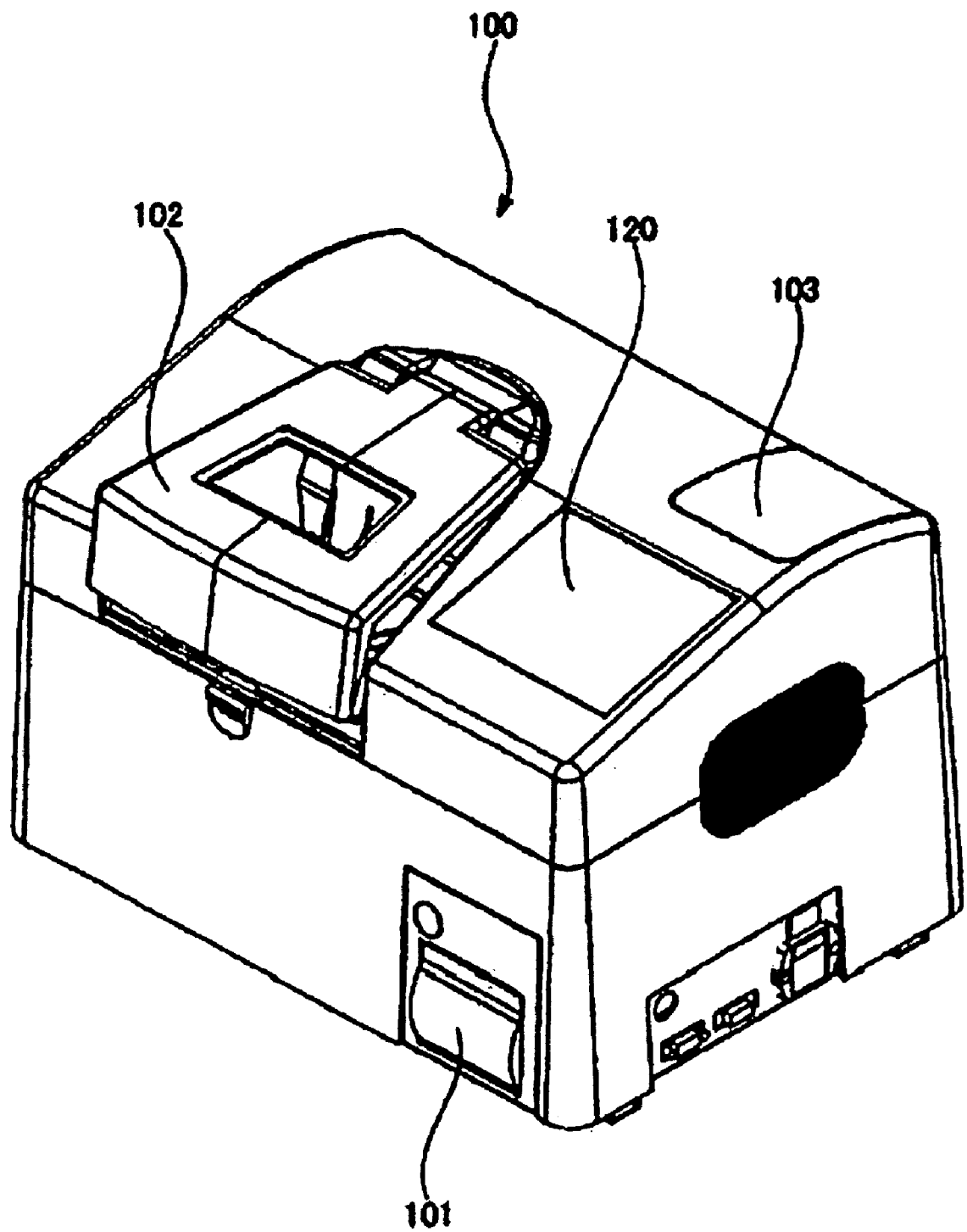
FIG. 1 is a perspective view showing one embodiment of a testing device of this invention.

FIG. 1 is a perspective view showing one example of the structures of the testing device 100 of this invention. The testing device 100 is equipped with a display unit 120, such as liquid crystal panel, etc., which displays the analysis results; an output mechanism 101 for outputting the analysis results on a paper; a microchip releasing flap unit 102, which opens upward for attaching and detaching the microchip; a flap unit 103 which opens upward for attaching/detaching the light source housing, when the light source housing, which contains the discharge lamp, is attached/detached. When the microchip or the discharge lamp is exchanged, the lid unit of each is opened by button operation, etc.

Figure 2:
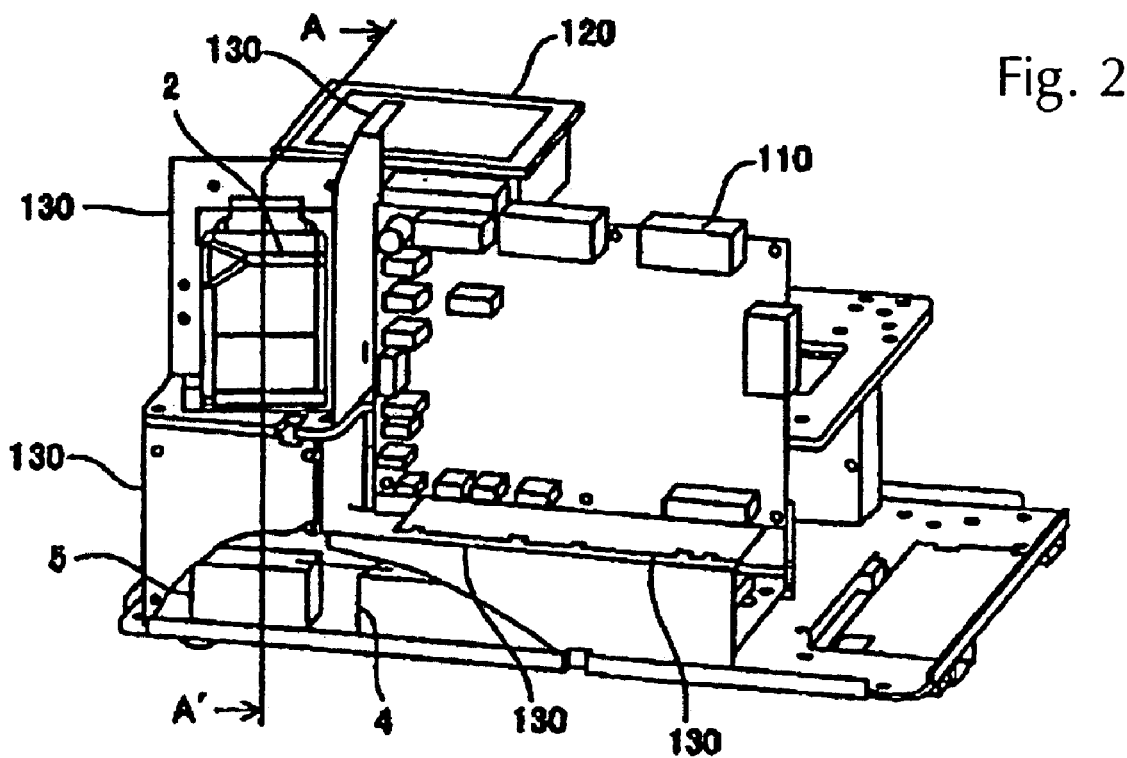
FIG. 2 is a perspective view showing one example of the inner structure of the testing device of this invention.
Figure 3:
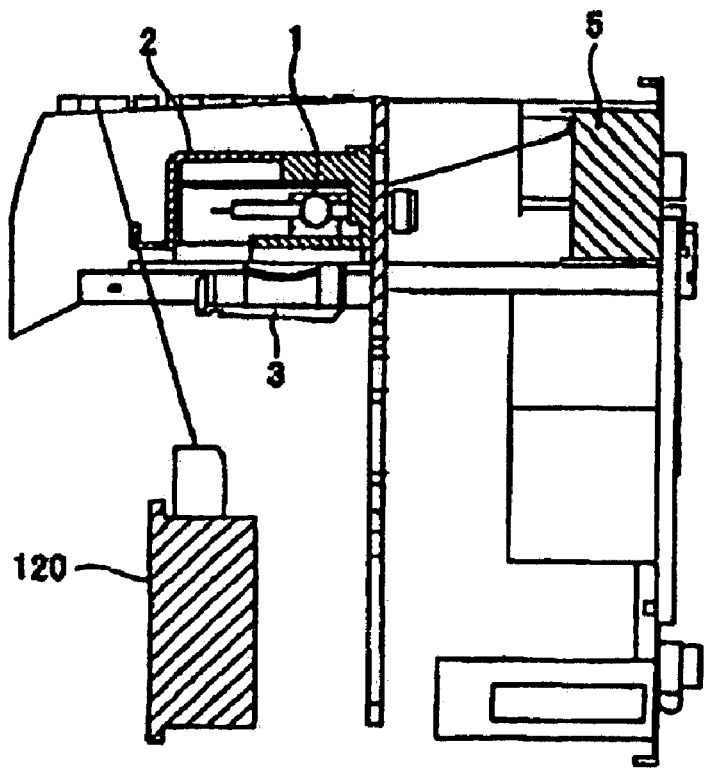
FIG. 3 is a cross-sectional view of the testing device taken along line A-A' in FIG. 2.

As shown in FIGS. 2 and 3, the testing device 100 comprises: a light source housing 2, in which the discharge lamp 1 is placed; a cooling air supply mechanism 3, which adjoins in the lower area in the vertical direction from the light source housing 2; a power supply 4 for the lamp and an igniter 5, which adjoin the lower area in the vertical direction from the light source housing 2; a chip holder 6 (not shown in FIG. 2); a microchip 7 (not shown in FIG. 2); an arithmetic computation unit 110, which adjoins the side of the light source housing 2; the display unit 120, which adjoins the side of the light source housing 2; and a shielding board 130, which adjoins the lower side in the vertical direction from the light source housing 2.

Figure 4:
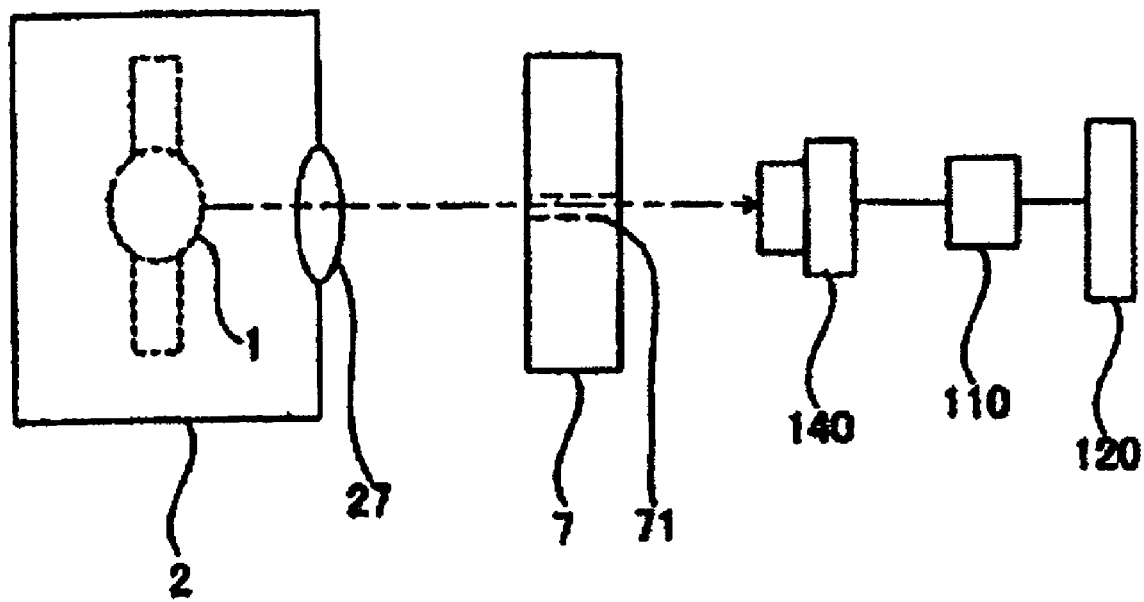
FIG. 4 is a conceptual diagram showing an overview of the absorbance determination system according to the testing device of this invention.

FIG. 4 is a conceptual diagram showing an overview of the absorbance determination system according to the testing device of this invention.

The testing device 100 comprises: the discharge lamp 1; light source housing 2, in which the discharge lamp 1 is contained; a lens 27 attached to the light source housing 2; the microchip 7 equipped with a test fluid receiver 71; a light receiving unit 140, which receives the light transmitted through the test fluid receiver 71 of the microchip 7; the arithmetic computation unit 110, which calculates the concentration of the test sample in the test fluid based on the optical intensity signal outputted from the light receiving unit 140; and the display unit 120, which displays the measurement result outputted from the arithmetic computation unit 110.

The light emitted from discharge lamp 1 penetrates through the lens 27 and enters into the test fluid receiver 71 of the microchip 7; then after being attenuated by the test fluid filled in the test fluid receiver 71, it is introduced into the optical entrance plane of the light receiving unit 140. The arithmetic computation unit 110 calculates the concentration of the components to be measured, which is contained in the test fluid, based on the intensity of the light introduced into the light receiving unit 140, and also sends the calculated data of the concentration of the components to be measured to the display unit 120. As a result, the concentration of the components to be measured is displayed on the display unit 120 as numerical data, etc.

Figure 5A:
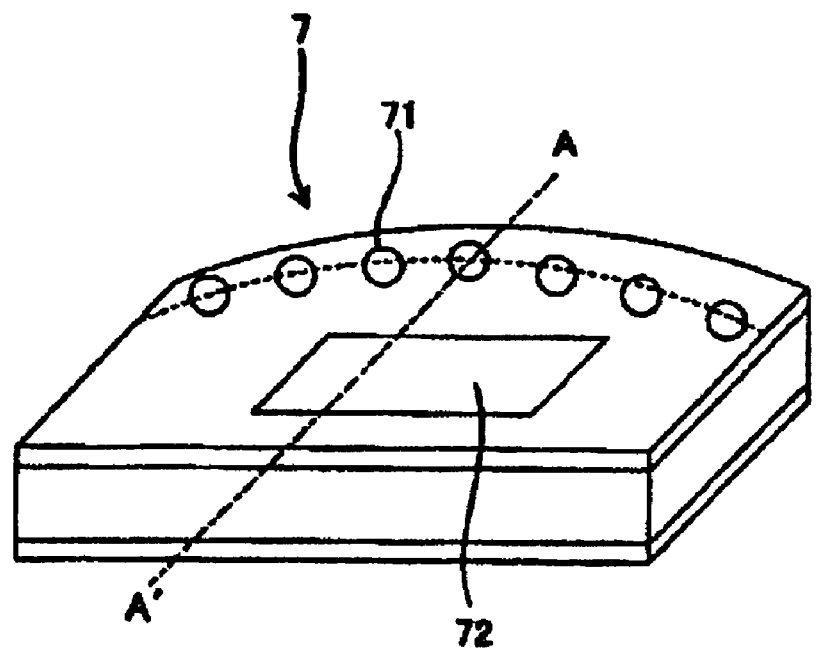
FIGS. 5(a) and 5(b) are a perspective view and a partial cross-sectional view, respectively, showing the structure of the microchip.
Figure 5B:
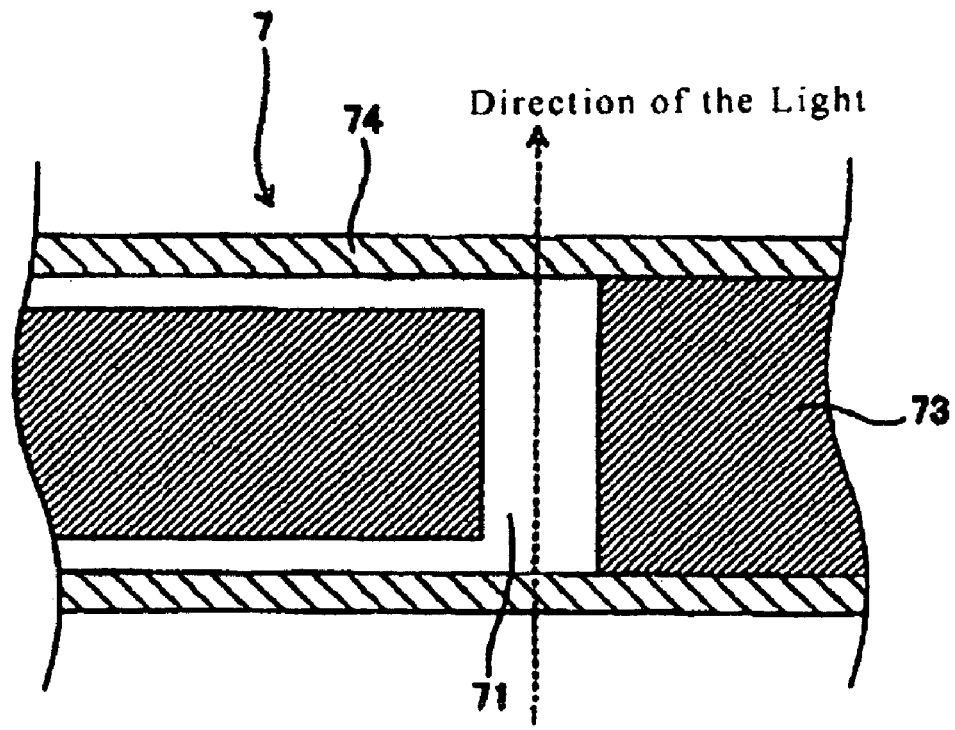
Figure 6:
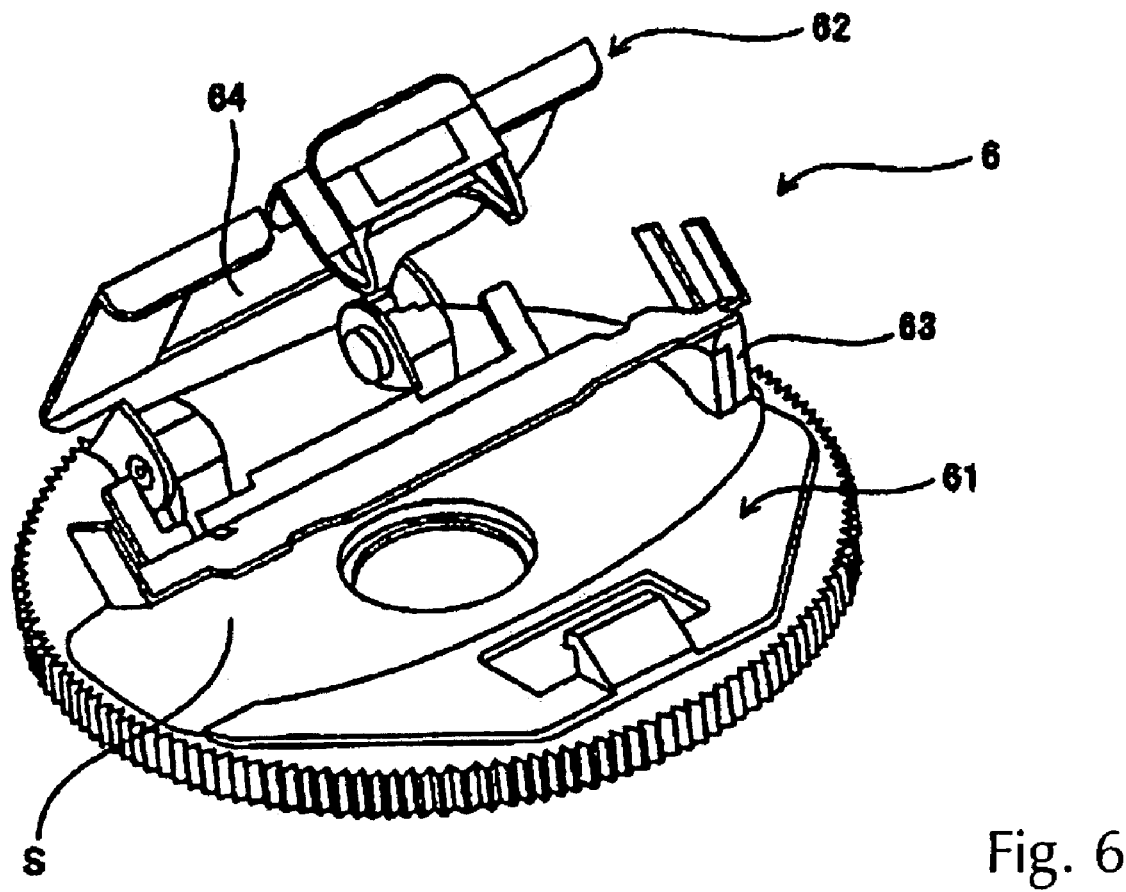
FIG. 6 is a perspective view showing the structure of the chip holder.

FIG. 5(a) is a perspective view of the microchip, and FIG. 5(b) shows a cross section taken along line A-A' in FIG. 5(a). FIG. 6 is a perspective view of the chip holder used in the microchip 2 shown in FIG. 5(a).

The microchip 7 shown in FIG. 5(a) is formed with two or more test fluid receivers 71, which are lined up in certain distance from each other and is a multiple-testing microchip, wherein a two-dimensional code 72 is attached to its outer surface. The multiple-testing microchip 7 is formed by attaching a light permeable resin 74 to the upper and lower surfaces of a light blocking resin 73, as shown in FIG. 5(b). Analyses using absorption photometry is then conducted by vertically transmitting the light through the test fluid receiver 71 of the microchip 7.

As shown in FIG. 6, the chip holder 6 is composed of a resin box unit 61, which has a chip containing space S, in which the microchip 7 is contained; and a metallic lid unit 62, which aligns and fixes the microchip 7 at a given position. The lid unit 62 is hinged to pivot and a code reading window 64 is installed in it to read the two-dimensional code 72 attached to the microchip 7.

Figure 8:
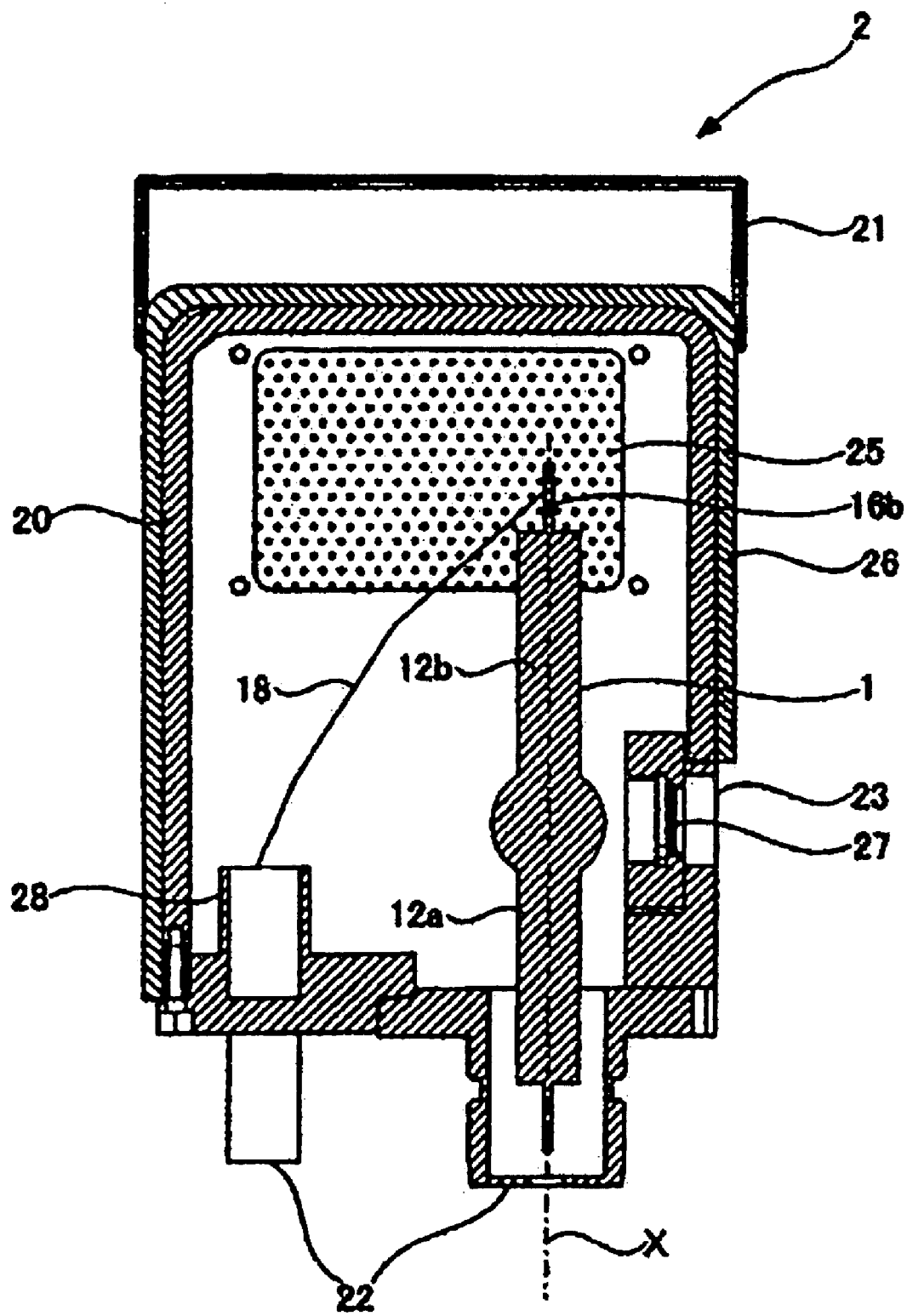
FIG. 8 is a cross-sectional view of the light source housing taken along the line A-A' in FIG. 7 looking towards the central axis of the discharge lamp.
Figure 9:
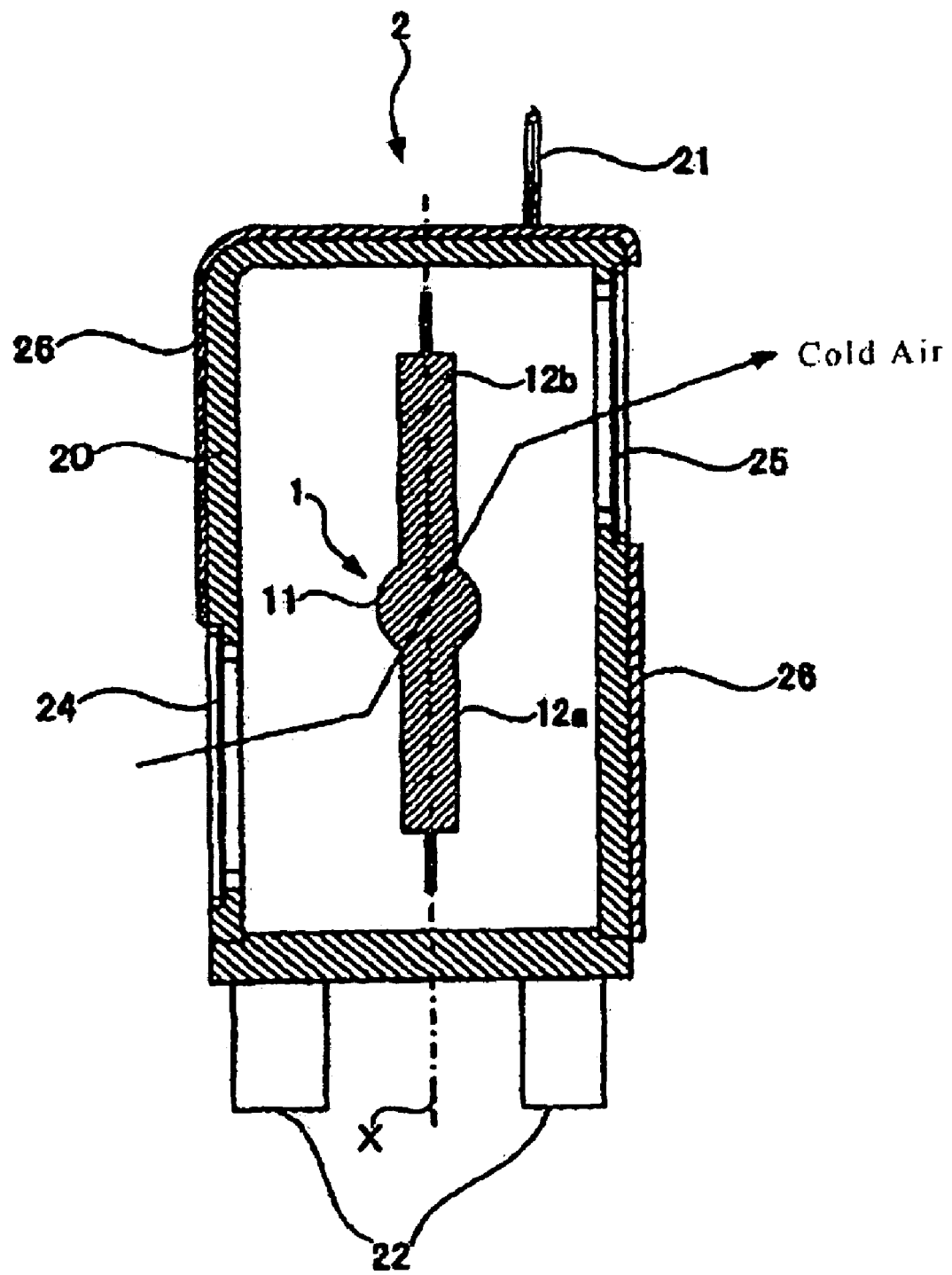
FIG. 9 is a cross-sectional view of the discharge lamp and the light source housing taken along the line B-B' in FIG. 7 looking towards the central axis of the discharge lamp.
Figure 10:
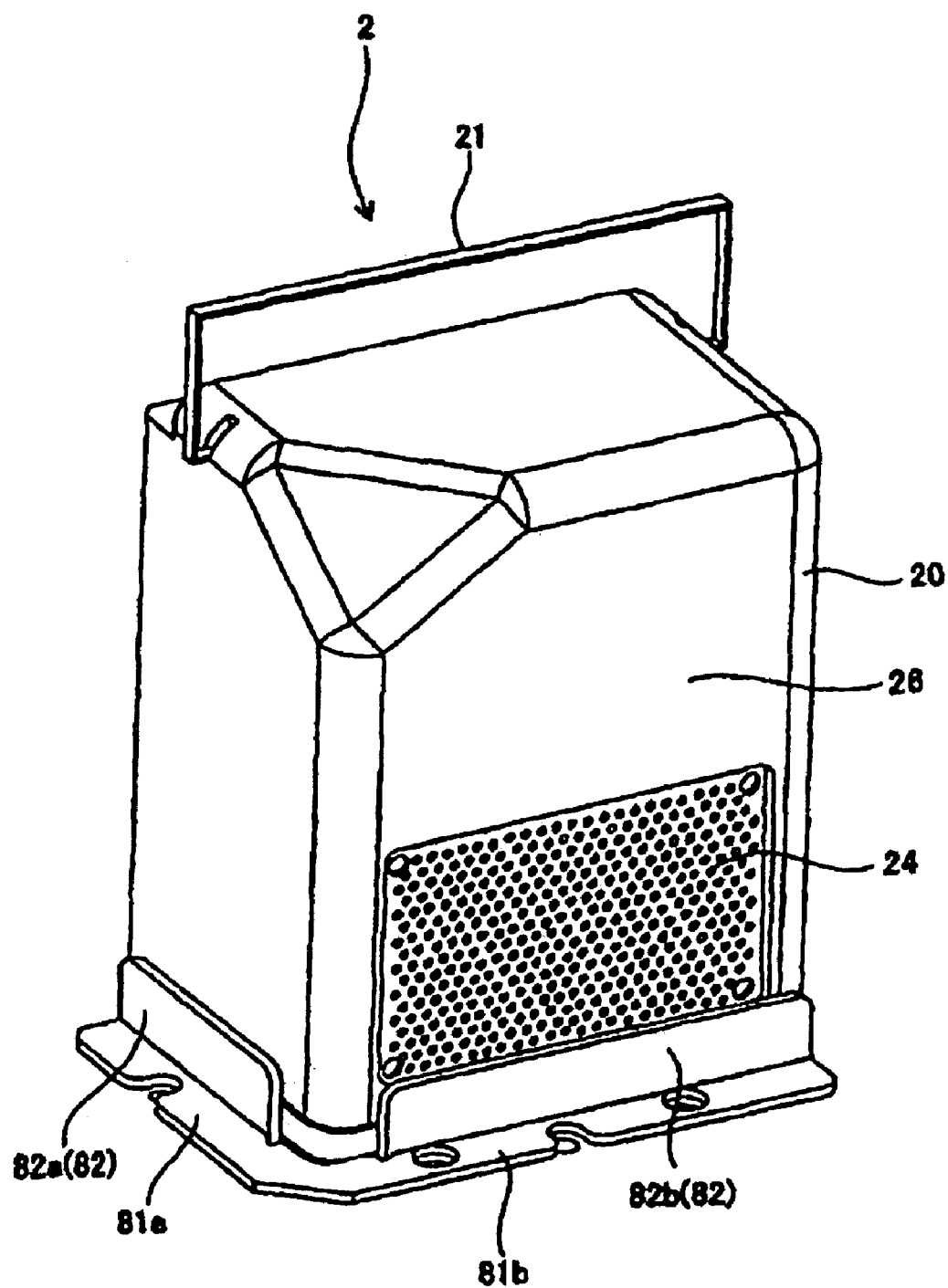
FIG. 10 is a perspective view showing the structure of the light source housing and the pressing mechanism.
Figure 11A:
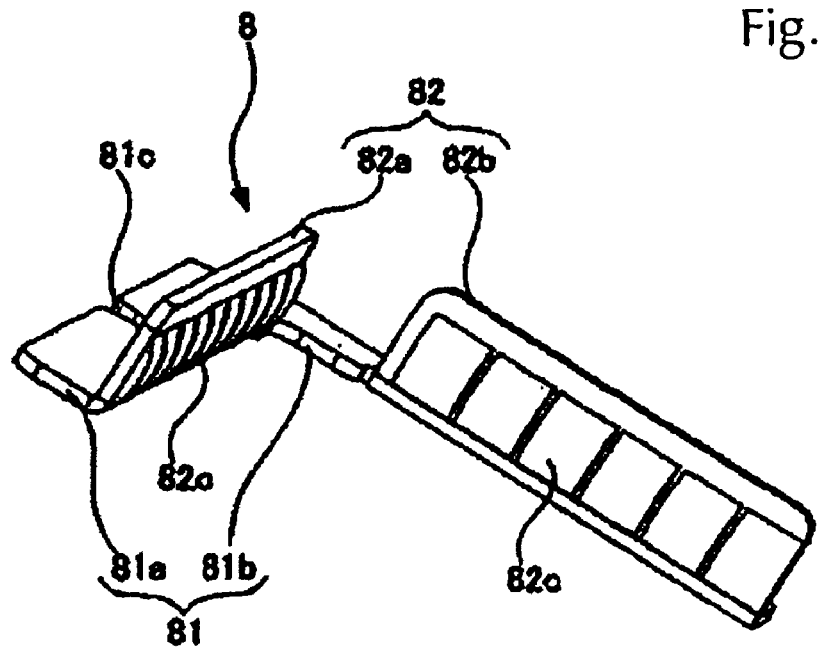
FIGS. 11(a) and 11(b) are diagrams showing the structure of the pressing mechanism.
Figure 11B:
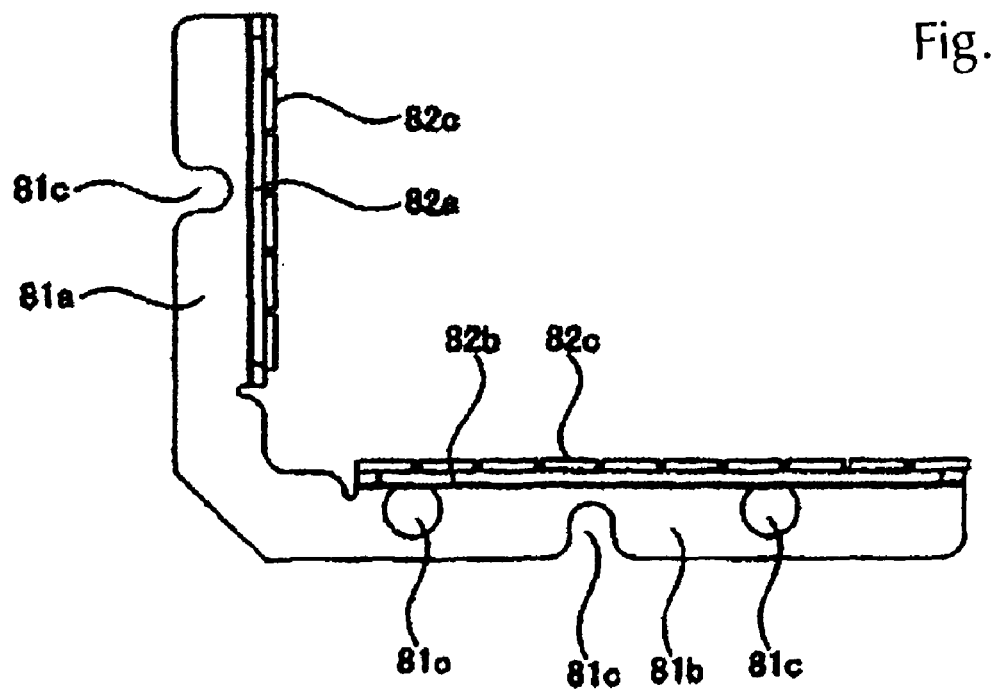
Figure 12:
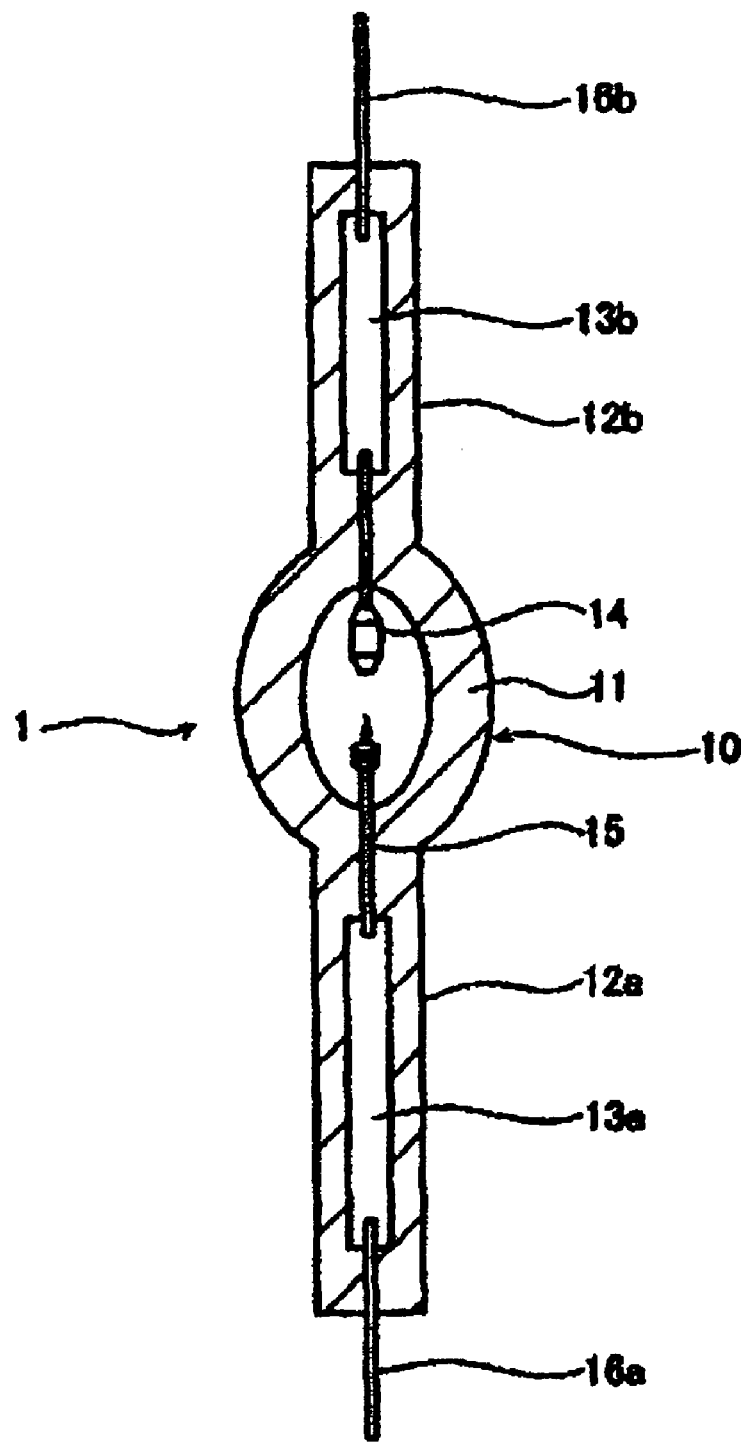
FIG. 12 is a cross-sectional view showing the longitudinal structure of the discharge lamp.

FIGS. 7(a)-(c) show an overview of the structure of the light source housing and the discharge lamp used in the testing device of this invention. FIG. 7(a) is a perspective view showing the top oblique view of the container unit of the light source; FIG. 7(b) shows a rear view of the container unit of the light source, and FIG. 7(c) is a top view of the light source housing. FIG. 8 is a cross-sectional view, obtained by cutting the discharge lamp and the light source housing along line A-A' shown in FIG. 7(c), in the direction of the central axis of the discharge lamp. FIG. 9 is a cross-sectional view in the direction of the central axis of the discharge lamp obtained by cutting the discharge lamp and the light source housing along line B-B' in FIG. 7(b). FIGS. 8 and 9 show that the discharge lamp 1 is located inside the light source housing 2 such that the central axis X of the discharge lamp 1 is perpendicular to the ground, i.e., is vertically oriented. FIG. 10 is a perspective view showing an overview of the structures of the light source housing and the pressing mechanism. FIG. 11(a) is a perspective view showing an oblique top perspective view of the pressing mechanism, and FIG. 11(b) is a top plan view of the pressing mechanism. FIG. 12 is a longitudinal cross-sectional view showing the structure of the discharge lamp 1.

As shown in FIGS. 7(a)-(c), the light source housing 2 comprises: a housing 20, which is composed of the rectangular shaped insulating material; a handle 21 to grasp when the light source housing 2 is to be moved; and a fixing mechanism 22, which is located vertically below the housing 20 to fix the light source housing 2 on the testing device 100 and to electrically connect the discharge lamp 1 to the igniter 5.

As shown in FIGS. 8 and 9, the housing 20 of the light source 2 comprises a light emitting unit 23, on the side surface of which the lens 27 to focus the light emitted from the discharge lamp 1 is inserted. In addition, a cooling air inlet 24, through which cooling air is introduced into the housing 20 of the light source 2, and a cooling air outlet 26, which discharges the cooling air outside of the housing 20 of the light source 2, are formed to efficiently cool down the discharge lamp 1.

The housing 20, which constitutes the main part of the light source 2, is required to be insulated from the discharge lamp 1, and it is desirable to be as small as possible as described above. Therefore, it is made of insulating materials, for example, highly heat resistant PPS resin. As used herein, the term "insulating materials" refers to materials which are electrically insulating. Also, the electromagnetic waves shielding mechanism made with a thin metal film 26 is formed on the outer surface of the housing 20 in order to shield the electromagnetic waves emitted around the discharge lamp 1. The thin metal film 26 is formed on the outer surface of the light source housing 2, because the housing 20 cannot be insulated from the discharge lamp 1 when the thin metal film 26 is formed on the inner surface of the housing 20, unless the housing 20 is large in size.

The thin metal film 26, which is functioning as the electromagnetic waves shielding mechanism, is formed on the outer surface of the housing 20 using well known methods, for example, by the vacuum deposition or the conductive coating of metal materials, such as aluminum. The thickness of the thin metal film 26 is preferably about, for example, 0.1 μm to 100 μm.

As shown in FIG. 10, the housing 20 of the light source 2 is fixed inside the testing device 100 by pressing the area on the outer surface of the housing 20, where the thin metal film 26 is formed, with a pressing mechanism, such as a metallic hook-shaped elastic body 8. The hook-shaped elastic body 8, for example, comprises two or more screw holes 81c, as shown in FIG. 11, to fix itself on the testing device 100 and is composed of the grounding unit 81, which is hook-shaped as a whole, and a pair of the pressing units 82, which extend perpendicular to the grounding unit 81. The grounding unit 81 is composed of: a base plate unit 81a, whose entire length is relatively short; a base plate unit 81b extending to a direction which perpendicularly intersects the base plate unit 81a, wherein the entire length of the plate unit is relatively long; and the screw hole 81c, which is formed on the base plate units 81a, 81b. Each of the pressing units 82 is composed of: a pair of the supporting plate units 82a, 82b extending vertically to each of the base plate units 81a, 81b; and a spring unit 82c, which curves in an arc towards the housing 20 of the light source 2, which is formed on each of the supporting plate units 82a, 82b The housing 20 of the light source 2 is positioned and fixed on the given place inside the testing device 100 in a way that the unit is pressed on the inside wall of the testing device 100 through the spring unit 82c of the hook-shaped elastic body 8 and two sides of the housing 20 of the light source 2 are attached to each pressing unit 82 of the hook-shaped elastic body 8. The hook-shaped elastic body 8 is attached in an area, which is the outer surface of the housing 20 and in which the thin metal film 26 is formed, as well as it is connected to ground. In this way, the housing 20 is grounded through the hook-shaped elastic body 8; therefore, the electromagnetic waves emitted around the discharge lamp 1 are discharged through the thin metal film 26 and the hook-shaped elastic body 8 formed on the housing 20. In order to shield the electromagnetic waves and discharge them through the hook-shaped elastic body 8, it is desirable that the thin metal film 26 is formed throughout the entire area of the outer surface of the housing 20 of the light source 2.

Within the testing device 100, the hook-shaped elastic body 8 is fixed to the position, where elastic power is added to two sides of the housing 20, through each of the spring units 82c by repelling force, which is generated by each spring unit 82c of the pair of pressing units 82, when the light source housing 2 is arranged. In this way, the side of the housing 20 can be pressed with the hook-shaped elastic body 8; thereby it is ensured that the light source housing 2 is grounded through the housing 20, as well as fixed in a predetermined position.

In addition, according to the above mentioned example, the housing 20 is connected to ground by pressing the area, in which the metal film 26 of the housing 20 is formed, with the hook-shaped elastic body 8; however, it is not necessarily essential to install the hook-shaped elastic body 8 in this invention. In other words, the ground line may be connected to the thin metal film 26 shown on the housing 20 in FIG. 8.

The metal film 26 is placed on the outer surface of the housing 20 in order to let the electromagnetic waves emitted around the discharge lamp 1 out; however, it is not necessarily essential to install the thin metal film 26 on the outer surface of the housing 20 in this invention. For example, the metal foil attached on the outer surface of the housing 20 may be connected to the ground.

As shown in FIG. 12, the discharge lamp 1, comprises a spherical light emitting part 11, a cylindrical hermetically sealed parts 12a, 12b, each of which is connected to a respective one of opposite sides of the light emitting part 11, and the lamp container 10 is made, for example, of a light transmissive material, such as quartz glass. The hermetically sealed parts 12a, 12b, have metal foils 13a, 13b made of molybdenum embedded therein.

Within the inner space of the light emitting part 11, an anode 14 and a cathode 16, whose rear end units are connected to a front end of the metal foils 13a, 13b, respectively, are placed with a defined gap between them in the direction of the central axis X. Also enclosed in the light emitting part 11 is xenon gas of about 0.5 MPa-2 MPa as a gas used for electric discharge. The rear end of outer lead wires 16a, 16b, which are connected to the metal foils 13a, 13b, at their front end, extend from the hermetically sealed parts 12a, 12b.

The discharge lamp 1, which is placed in a way that the light emitting part 11 is located near the lens 27 inserted in the light emitting unit 23 of the light source housing 2, is electrically connected to a connector 28 of the light source housing 2 through the aforementioned feed wire 18, wherein one of the hermetically sealed parts, 12a, is inserted and fixed inside a conductive fixing mechanism 22 of the light source housing 2, as well as the feed wire 18 is connected to the outer lead wire 16b extended from the other hermetically sealed part 12b. The discharge lamp 1 is electrically connected to the above mentioned power supply 4 for the lamp through the fixing mechanism 22 and the connector 28, which are electrically conductive.

As shown in FIGS. 8 and 9, the discharge lamp 1 is installed inside the light source housing 2 in a way that the anode is located in the upper vertical area and the central axis X is perpendicular to the ground. By placing the discharge lamp in this way, as described below, there may be no risk that the discharge lamp may explode.

If the discharge lamp 1 is turned on in a position where the central axis X of the discharge lamp 1 is horizontal to the ground, the discharge arc formed may be deflected to the upper inner surface side of the light emitting unit 11 because of the convection currents of the discharge gas inside the light emitting unit 11. Therefore, only the upper part of the emitting unit 11 may reach a high-temperature, and in the worst case, there is a possibility that the light emitting unit 11 may explode. On the other hand, when the discharge lamp is turned on in a position where the central axis X of the discharge lamp is perpendicular to the ground, i.e., is vertical, the discharge arc formed will not be deflected to one part of the light emitting unit 11. Therefore, it can be avoided for only one part of the light emitting unit to be heated to a high temperature and there will be no possibility for it to explode.

A discharge lamp using xenon gas as discharge gas as described above; a super-high pressure mercury lamp, which is preferably used as the light source for projectors, and whose mercury vapor pressure, when the lamp is turned on, is 150 atmospheres or above when used for the testing device of this invention 100; a short arc type metal halide lamp; and a xenon flash lamp may be used as the discharge lamp used for the testing device 100 of this invention. Especially when the discharge lamp enclosing the above mentioned xenon gas in it is used, absorbance determination may be performed accurately, since the brightness can be easily increased by using a point light source; it has a continuous spectrum in a wide wavelength range of from 250 to 1100 nm; emission lines will not be generated especially in the wavelength range used to measure the light absorbance (more specifically, the wavelength ranging of from 300 to 800 nm); and a stable emission spectrum can be obtained.

As described above, in the testing device of this invention, for example, the light must be emitted into an extremely narrow light path, such as the test fluid receiver 71 of the microchip 7. Therefore, it is desirable to use a discharge lamp 1 with high brightness in order to increase the accuracy of measurements. In other words, the rated wattage of the discharge lamp 1 is preferably in the range, for example, from 20 to 150 W, more preferably, in the range from 40 to 60 W.

Next is the explanation of the cooling air inlet 24 and the cooling air outlet 25 installed in the housing 20 of the light source housing 2 referring back to FIGS. 8 and 9. The cooling air inlet 24 and the cooling air outlet 25 are formed in the housing 20 as described below. The cooling air inlet 24 and the cooling air outlet 25 are formed as openings in the metal walls of the housing 20 in a way that openings having relatively large areas are formed on the side surface thereof, and a metal plate, which has two or more fine openings, is screwed on to cover the aforementioned openings.

As described above, the light source housing 2 is smaller relative to the discharge lamp 1 and the housing 20 is formed of an insulating material; therefore, it is thought that the temperature of the internal space of light source housing 2 will easily be higher when the discharge lamp 1 is turned on as compared to when the housing is made of metal. In addition, in the discharge lamp 1 shown in FIG. 12, when the temperature of the hermetically sealed parts 12a, 12b becomes excessively high, it is possible that they may be damaged, and may be less airtight when the temperature of the hermetically sealed parts 12a, 12b becomes excessively high. Therefore, it is desirable to cool down the hermetically sealed parts 12a, 12b of the discharge lamp 1 by introducing cooling air into the housing 20 of the light source 2.

The housing 20 of the light source 2 is placed in an upper vertical area in a way that the cooling air inlet 24 is closer to the hermetically sealed part 12a and the cooling air outlet 25 is closer to the hermetically sealed part 12b. In other words, the cooling air inlet 24 and the cooling air outlet 25 are formed in a lower vertical area and an upper vertical area, respectively, of the housing 20 of the light source 2. In this way, cooling air introduced into the light source housing 2 may pass through near each of the hermetically sealed parts 12a, 12b of the discharge lamp 1, and so that the temperature of each of the hermetically sealed parts 12a, 12b will not become extremely high when the discharge lamp 1 is turned on.

In the above mentioned the light source housing 2, the cooling air inlet 24 is located in the lower vertical area of the housing 20, thereby cooling air introduced from the cooling air inlet 24 is warmed by the light emitting unit 11 when it passes through the housing near the light emitting unit 11, which becomes hotter when the discharge lamp 1 is turned on, and is discharged from the housing 20 through the cooling air outlet 25 by a convection current. This way, it is possible to efficiently cool down the discharge lamp 1.

According to the above mentioned housing 20, the cooling air inlet 24 and the cooling air outlet 25 are formed on opposite sides of the housing 20. The diameter of the openings formed on the metal plate covering the inlet and outlet openings 24, 25, is determined according to the correlation between the velocity and the frequency of the electromagnetic waves. There is a possibility that the electromagnetic waves emitted around the discharge lamp 1 may not be shielded if the diameter of the openings formed in the metal plate is too big and the discharge lamp may explode when strong impact is applied to it; therefore, it is desirable that the diameter of the openings is from about 1 mm to 10 mm to ensure the function to prevent the light transmissive materials, such as quartz glass, which constitute the discharge lamp, from shattering.

The following is the detailed explanation of other structures of the testing device of this invention 100 referring to FIG. 4.

The light receiving unit 140 has a function to receive the light passed through the test fluid, which is filled in the test fluid receiver 71 of the microchip 7, and to output light intensity signals according to the received light. For example, devices, such as silicon photo diodes, which have sensitivity to light having a wavelength in the range of 300 nm to 1000 nm, may be used for the light receiving unit 140.

The arithmetic computation unit 110 is connected to the light receiving unit 140. The arithmetic computation unit 110 has an arithmetic calculation mechanism to calculate the concentration of the component of the test sample in the test fluid by the Lambert-Beer law according to the light intensity signals output from the light receiving unit 140.

The display unit 120 functions to display the analysis results regarding the concentration of the components of the test sample output from the arithmetic computation unit 110 as data, such as numerical data, etc., and for example, it comprises a display device, such as liquid crystal panel, etc.

In a testing device 100 in accordance with the invention, the light, which is emitted from the discharge lamp 1 and made parallel by the lens 27 installed in the light source housing 2, is introduced into the test fluid receiver 71 of the microchip 7. Part of the light introduced to the test fluid receiver 71 is absorbed by the components of the test sample contained in the test fluid, part of the light, which was not absorbed, is introduced to the light receiving unit 140. Then, the electrical signal, which is converted by the photoelectric conversion of the average intensity of the received light, is output from the light receiving unit 140 as the light intensity signal to be input into the arithmetic computation unit 110. The concentration of the components of the test sample in the test fluid is then calculated and displayed on the display unit 120.

In the testing device 100 of this invention, as described above, the effects explained below may be expected, since the light source housing 2, which contains the discharge lamp 1, is made of insulating materials, and the shielding mechanism comprising the thin metal film 26 connected to ground is installed outside the housing 20 of the light source housing 2. In other words, by making the housing 20 of insulating material, it is possible to insulate the housing 20 from the discharge lamp 1 even when a relatively small-sized housing 20 is used in the discharge lamp 1.

Also, even if electromagnetic waves are emitted from the discharge lamp 1 when the discharge lamp 1 is turned on, the electromagnetic waves are released through the thin metal film 26 connected to the ground; therefore it is possible to avoid malfunctioning of the precision apparatus inside the testing device 100 (for example, the arithmetic computation unit 110, etc.) for sure.

Moreover, it is possible to reduce the size of the testing device 100 by forming the shielding mechanism, which comprises the thin metal film 26, on the outer surface of the housing 20 as compared to installing a shielding mechanism separately from the housing 20 since this feature of the invention makes it unnecessary to provide extra space inside the testing device 100.

Additionally, it is possible to securely connect the thin metal film 26 of the housing 20 to the ground and to place the light source housing 2 in the predetermined position inside the testing device 100 since the outer surface of the housing 20, which is also the area where the metal film 26 is formed, is pressed by the pressing mechanism, such as the hook-shaped elastic body 8 connected to the ground.

Furthermore, it is possible to prevent the housing 20 from melting even when the housing 20 is made of an insulating material, which has less heat resistance as compared to metallic materials, since the cooling air supply mechanism 3, as well as the cooling air inlet 24 and the cooling air outlet 25 are provided.

Furthermore, it is possible to prevent the light emitting unit 11 from being damaged by the discharge lamp 1 oriented in a way that its central axis X is vertical.

Moreover, the cooling air inlet 24 is installed opposite the hermetically sealed part 12a, which is located vertically at the lower end of the discharge lamp 1 and the cooling air outlet 25 is located opposite the hermetically sealed part 12b, which is located vertically at the top of the discharge lamp 1. Therefore, each of the hermetically sealed parts 12a 12b in the discharge lamp 1 can be cooled down and kept from being in excessively high temperature; thereby it is possible to prevent each of the hermetically sealed parts 12a, 12b from being damaged.

The testing device 100 of this invention is not limited to the above mentioned embodiments and various changes may be added to it without departing from the nature and the scope of the present invention. Also, the shapes of the chip holder 6 and the microchip 7 according to the above mentioned embodiments are intended to be exemplary only and suitable modifications may be added as necessary.

What is claimed is:

1. A testing device, comprising:
   a microchip having a receiver for test fluid;

a light source having a discharge lamp which emits light into the test fluid receiver, the light source having a housing in which the discharge lamp is located;

a light receiving unit which receives the light transmitted through the test fluid receiver, and an arithmetic calculation mechanism which calculates a concentration of a component of the test fluid to be detected based on the intensity of light emitted from the test fluid receiver after having passed through the test fluid therein and received by the light receiver, wherein the discharge lamp has a rated power of 20 W to 150 W, and wherein the light source housing is formed of an electrical insulating material and is equipped on an outer surface thereof with a shielding mechanism connected to the ground comprised of a thin metal film having a thickness of 0.1 µm to 100 µm, the shielding mechanism shielding the arithmetic calculation mechanism located outside of the housing from electromagnetic waves emitted from the light source.

2. The testing device according to claim 1, wherein the testing device is equipped with a pressing mechanism which presses an area in which the thin metal film is formed on the outer surface of the light source housing.

3. The testing device according to claim 2, wherein the pressing mechanism is connected to ground.

4. The testing device according to claim 1, wherein the testing device is equipped with a cooling air supply mechanism for supplying cooling air into the light source housing, and wherein a cooling air inlet and a cooling air outlet are formed in the light source housing.

5. The testing device according to claim 4, wherein the light source is a discharge lamp equipped with a light emitting part in which a pair of electrodes and a discharge gas are contained, wherein a hermetically sealed part is attached to each of opposite sides of the light emitting part, and wherein a central axis of the discharge lamp is vertically oriented.

6. The testing device according to claim 5, wherein the cooling air inlet is located opposite the hermetically sealed part which is located at a vertically lower end of the vertically oriented discharge lamp, and the cooling air outlet is located opposite the hermetically sealed part which is located at a vertically upper end of the vertically oriented discharge lamp.

7. The testing device according to claim 1, wherein the light source housing is located within an enclosure of the testing device which has an output unit which outputs analysis results; a microchip unit for attaching and detaching of the microchip; and a flap unit with an opening through which the light source housing is insertable and removable for attaching and detaching thereof from the enclosure.

* * * * *